(12) United States Patent
Morley et al.

(10) Patent No.: US 8,795,187 B2
(45) Date of Patent: Aug. 5, 2014

(54) DEVICE AND PROCESS FOR RECOGNIZING A CORRECT USE OF AN ALCOHOL MEASURING DEVICE

(75) Inventors: Stefan Morley, Lübeck (DE); Ulrich Köhler, Bad Oldesloe (DE); Andreas Huth, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 445 days.

(21) Appl. No.: 12/546,144

(22) Filed: Aug. 24, 2009

(65) Prior Publication Data

US 2010/0251804 A1 Oct. 7, 2010

(30) Foreign Application Priority Data

Sep. 2, 2008 (EP) ..................... 08163527
Apr. 3, 2009 (EP) ..................... 09157268

(51) Int. Cl.
*A61B 5/08* (2006.01)
*B60K 28/06* (2006.01)
*G01N 33/98* (2006.01)
*G01N 33/497* (2006.01)

(52) U.S. Cl.
USPC ........... 600/532; 180/272; 340/576; 382/115; 73/23.3

(58) Field of Classification Search
USPC .................. 600/532, 543, 300; 382/115–127; 340/5.6, 5.8, 5.82–5.83, 575–576; 348/333.01–333.02; 180/272; 73/23.3
See application file for complete search history.

(56) References Cited

U.S. PATENT DOCUMENTS

| | | | | |
|---|---|---|---|---|
| 4,916,435 A * | 4/1990 | Fuller | ........................ | 340/573.4 |
| 6,075,445 A * | 6/2000 | McLoughlin et al. | ........ | 340/586 |
| 6,433,863 B1 * | 8/2002 | Weiss | ................. | 356/72 |
| 6,748,792 B1 * | 6/2004 | Freund et al. | ................... | 73/23.3 |
| 7,432,973 B2 * | 10/2008 | Iga | ........................... | 348/333.03 |
| 7,823,681 B2 * | 11/2010 | Crespo et al. | ................. | 180/272 |
| 7,864,990 B2 * | 1/2011 | Corcoran et al. | ............. | 382/118 |
| 2004/0100572 A1 * | 5/2004 | Kim | ........................ | 348/333.01 |
| 2006/0274936 A1 | 12/2006 | Ohkubo et al. | | |
| 2008/0013799 A1 * | 1/2008 | Steinberg et al. | ............. | 382/118 |
| 2008/0069403 A1 | 3/2008 | Breed | | |
| 2008/0170762 A1 | 7/2008 | Endo et al. | | |
| 2009/0090577 A1 * | 4/2009 | Takahashi et al. | ............ | 180/272 |
| 2009/0169068 A1 * | 7/2009 | Okamoto | ....................... | 382/118 |
| 2009/0169069 A1 * | 7/2009 | Kim et al. | ..................... | 382/124 |
| 2010/0012417 A1 * | 1/2010 | Walter et al. | ................. | 180/272 |
| 2011/0084820 A1 * | 4/2011 | Walter et al. | ............. | 340/426.24 |

FOREIGN PATENT DOCUMENTS

EP 0 172 169 2/1986
EP 1 591 296 A1 11/2005

* cited by examiner

*Primary Examiner* — Navin Natnithithadha
*Assistant Examiner* — Eric Messersmith
(74) *Attorney, Agent, or Firm* — McGlew and Tuttle, P.C.

(57) ABSTRACT

A device and a process are provided for recognizing a correct use of an alcohol measuring device by a test subject. At least one alcohol measuring device is provided with a signal transmitter, an analysis and control unit and a camera unit. An image field of the camera unit is divided into an inner image field area and an outer image field area. The inner image field area detects at least the face area of the test subject. The camera unit records changes at a boundary between the inner image field area and the outer image field area. A signal sent by the signal transmitter in the inner image field area can be detected by the camera unit.

20 Claims, 5 Drawing Sheets

DEVICE AND PROCESS FOR RECOGNIZING A CORRECT USE OF AN ALCOHOL MEASURING DEVICE

CROSS REFERENCE TO RELATED APPLICATIONS

This application claims the benefit of priority under 35 U.S.C. §119 of European Patent Application EP 09 157 268.5 filed Apr. 3, 2009, the entire contents of which are incorporated herein by reference.

FIELD OF THE INVENTION

The present invention pertains to a device and a process for recognizing a correct use of an alcohol measuring device by a test subject with the device including at least an alcohol measuring device, an analysis and control device and a camera unit.

BACKGROUND OF THE INVENTION

Alcohol measuring devices are used especially in the combination with a vehicle immobilizer of a vehicle, a so-called "interlock system." An interlock system comprises essentially two components: the alcohol measuring device, which is located in the interior space of the vehicle, as well as a control device, which is installed, as a rule, under the dashboard and establishes or blocks the power supply to a starting relay of the vehicle. After the vehicle ignition has been turned on, the interlock system asks the operator to provide a breath sample. The measurement result for the alcohol concentrations decides whether the starter of the vehicle is released and the engine can thus be started. Manipulation is possible, in principle, during the use of the interlock system based on an alcohol measurement by a second person, who is not the driver. To rule out such a possibility of circumvention, an interlock system usually has an alcohol measurement repeat function. Such a repeated measurement is required from the driver, for example, after a time interval generated according to the random principle. Yet, there is a possibility of multiple alcohol measurements by a second person who is not steering the vehicle.

An interlock system, which comprises a video camera, which selectively stores pictures, with a position sensor, which ensures that the video camera correctly detects the tester, is known from EP 1 591 296 A1. The video image is stored and can be sent to an analysis center for identification. The drawback of this device is, however, that identification of the tester takes place with a time delay or a comparison with a picture of the tester imposes high requirements on image processing.

SUMMARY OF THE INVENTION

Based on the state of the art, the object of the present invention is to improve a device, which prevents a vehicle, a machine or an access barrier from being put into operation by a human operator who is under the influence of alcohol, such that the safety against manipulation is increased.

This object is accomplished by a device and a process for recognizing a correct use of an alcohol measuring device by a test subject with at least one alcohol measuring device with a signal transmitter, an analysis and control unit and a camera unit. The image field of the camera unit is divided into an inner image field area and an outer image field area, wherein the inner image field area registers or gathers (detects) at least the area of the face of the test subject, wherein the alcohol measuring device is provided with a signal transmitter and the camera unit is set up to detect a signal sent by the signal transmitter in the inner image field area, and the analysis and control unit is set up to analyze this sent signal.

Based on the detection and analysis of the signal, it is recognized with the device according to the present invention whether the alcohol measuring device is located in the inner image field area of the camera unit. The camera unit is set up such that the inner image field area of the camera unit detects at least the area of the face of the test subject. It can thus be ensured that the alcohol measuring device is located in the area of the sampling site during the alcohol measurement.

The camera unit is advantageously designed as an infrared camera, the infrared camera preferably operating in a spectral range of 450-1,050 nm. The sensitivity of the camera is at a quantum efficiency of more than 10%. As a result, use in both daylight and with active, invisible illumination in the infrared spectral range is possible. The signal transmitter provided at the alcohol measuring device is designed to send an infrared signal, which preferably blinks alternatingly. The functionality of the device according to the present invention can be guaranteed by the use of an infrared camera and an infrared light signal to be detected by the infrared camera even under poor light conditions and in darkness.

As an alternative to this, a camera unit for a visible spectral range may be used, which can detect an optical light signal of the signal transmitter in the inner image field area, the optical light signal preferably blinking alternatingly in red and yellow.

In yet another advantageous embodiment of the device according to the present invention, the signal transmitter may be designed as a light-reflecting element, to which a light signal of a light source is sent, wherein the reflected light can be detected by the camera unit in the inner image field area.

In yet another preferred embodiment, the alcohol measuring device is designed as a breath alcohol measuring device, which measures the alcohol content in a breath sample provided by the test subject. Furthermore, the alcohol measuring device may be an alcohol measuring device, which is designed as a portable device and as a device that can be attached to a body part of the user, preferably to the arms, and which measures an alcohol content by means of a gas sensor measuring the skin permeation.

In another advantageous embodiment of the device according to the present invention, the camera unit is set up to detect motions from the inner image field area to the outer image field area and/or from the outer image field area to the inner image field area. The analysis and control unit is set up, furthermore, to analyze these motions. The inner image field area and preferably the outer image field area of the camera unit may have an oval shape. An oval shape, for example, the shape of an ellipse, is suitable for detecting the test subject in its longitudinal axis by means of the camera unit. Furthermore, the oval shape makes possible a more favorable scalability.

The device according to the present invention makes it possible to reduce the hazard potential of a human operator who is under the influence of alcohol in a safety-relevant means by increasing the safety against manipulation of an alcohol measurement.

The device according to the present invention may be used in access control for safety-relevant means, in an interlock system for starting a vehicle, boat or aircraft after an alcohol measurement and even for releasing a control panel of a machine.

The present invention will be explained in more detail with reference to the drawings attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
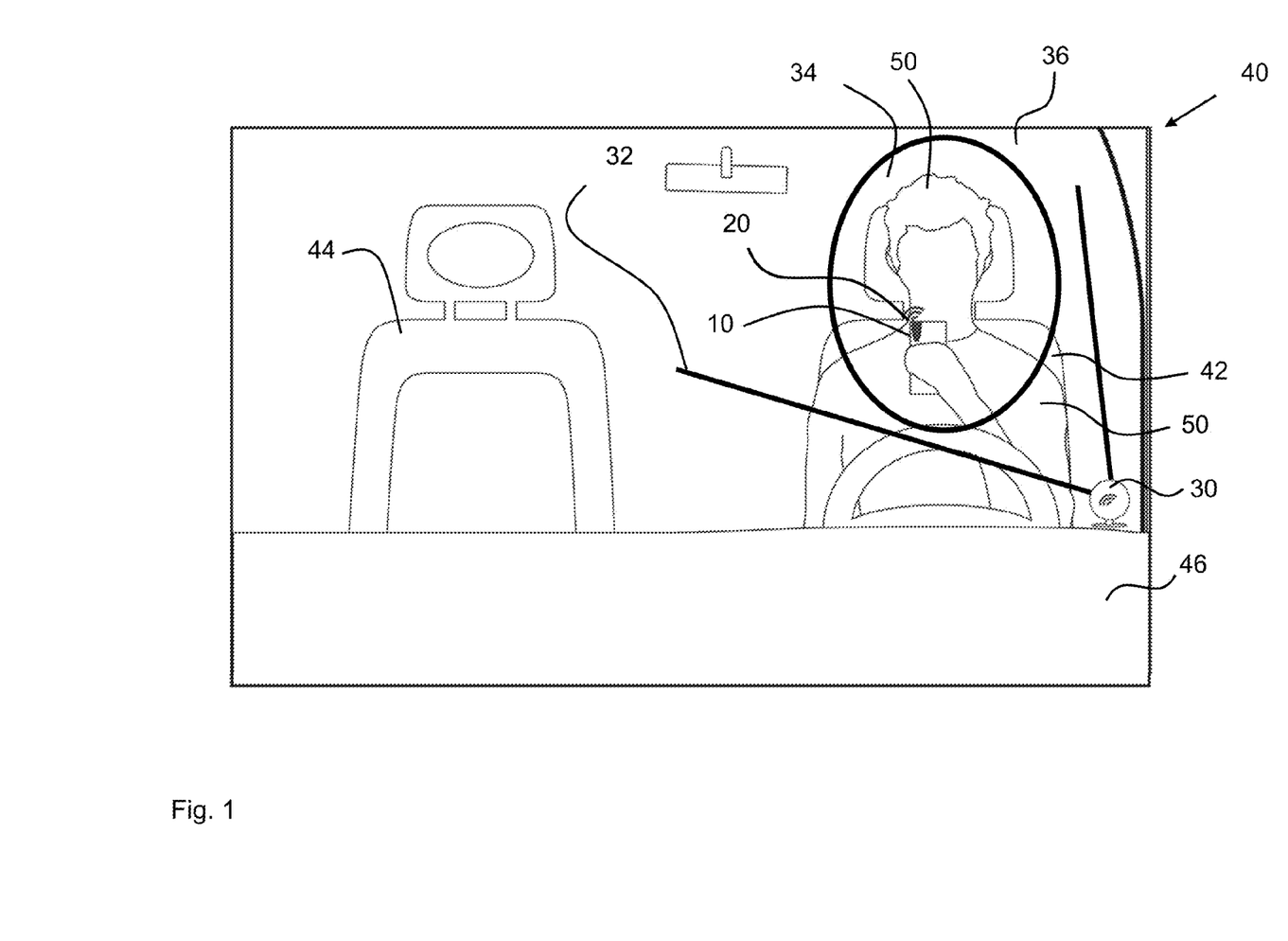
FIG. 1 is a schematic view of a first embodiment of the device according to the present invention in a vehicle.
Figure 5:
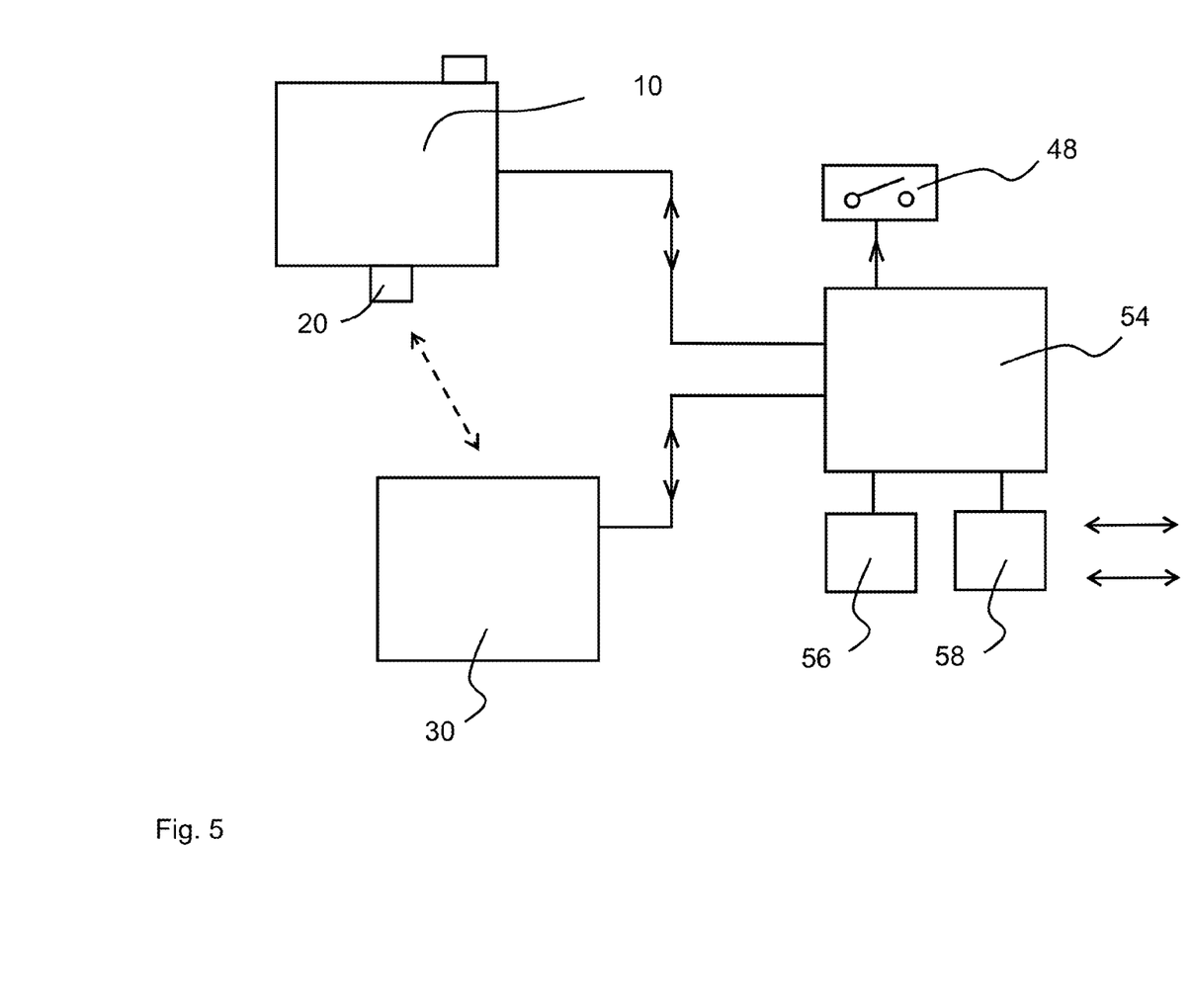
FIG. 5 is a block diagram of the device according to the present invention in an interlock system.

Referring to the drawings in particular, FIG. 1 shows a device according to the present invention for recognizing a correct use of an alcohol measuring device 10 by a test subject 50 combined with an interlock system in a vehicle 40. FIG. 1 shows the front view of the vehicle 40 with a driver's seat 42 and with a front passenger seat 44. The interlock system comprises an alcohol measuring device 10 and an analysis and control device 54 (block diagram in FIG. 5), which is located under a dashboard 46. The analysis and control device 54 is provided, among other things, for releasing or blocking the power supply to a starter relay of the vehicle 40. The alcohol measuring device 10 is designed as a breath alcohol measuring device, which measures the alcohol content in a breath sample provided by the test subject 50. The measurement result for the breath alcohol concentration decides on whether a starting means 48 (block diagram in FIG. 5) of the vehicle 40 is released and the engine can thus be started. A camera unit 30 arranged on the dashboard 46 has an image field 32, which is divided into an inner image field area 34 and an outer image field area 36. The camera unit 30 is arranged on the dashboard 46 such that the inner image field area 34 detects at least the area of the face of the test subject 50. The test subject 50 is sitting on the driver's seat 42 for the alcohol measurement. The camera of the camera unit 30 is designed as an infrared camera. The spectral range of the infrared camera is in a range of 450 nm to 1,050 nm, at a quantum efficiency of more than 10%. This makes it possible to use the camera unit 30 both in daylight and with invisible illumination in the infrared spectral range.

The alcohol measuring device 10 has, furthermore, a signal transmitter 20, which sends a signal during or before an alcohol measurement, and a signal sent by the signal transmitter 20 in the inner image field area 34 can be detected by the camera unit 30. An analysis and control unit 54 (shown in FIG. 5) is set up to analyze this sent signal. The signal transmitter 20 of the embodiment variant shown in FIG. 1 sends an infrared signal, which is switched alternatingly on and off and can be detected by the camera unit 30 designed as an infrared camera. A signal modulation of the infrared signal by alternating switching on and off increases the reliability of the device according to the present invention. A reproduced model of an alcohol measuring device with a signal transmitter provided would thus be recognized by the system. Furthermore, it is ensured in this step of the alcohol measurement with the device according to the present invention that the alcohol measuring device is located in the area of the sampling site, namely, in the area of the driver's seat, during the alcohol measurement.

Furthermore, it can be ensured with the device according to the present invention in a previous step that no other person is located in the area of the driver's seat 42. A number of persons is detected for this by the camera unit 30 in the inner image field area 34, and a signal is sent if more than one person is detected in the inner image field area 34. An image of the inner image field area is detected and stored by the camera unit 30 in an advantageous manner.

Both the alcohol measuring device 10 and the camera unit 30 are connected to the analysis and control unit 54. After actuation of the starting means 48 of the vehicle 40, the interlock system signals to the test subject 50 the beginning of an alcohol measurement. The camera unit 30 is activated and it monitors the presence of the infrared signal within the inner image field area 34 in the inner image field area 34. If no infrared signal is recognized by the camera unit 30 within the inner image field area 34, a new alcohol measurement can be requested by the interlock system.

As an alternative, it is also possible for the camera unit 30 to go into standby with the actuation of the starting means 48 of the vehicle 40 by the test subject 50, but is activated only after an acknowledgment at the alcohol measuring device 10, for example, by actuating an activating button provided on the alcohol measuring device 10.

In another embodiment of the device according to the present invention, the camera unit is set up to record all changes within the inner image field area 34 and at least partly within the outer image field area 36 at the beginning of the alcohol measurement. Changes in a boundary area 38, for example, due to a motion of the test subject 50, from the inner image field area 34 into the outer image field area 36 or of another person from the outer image field area 36 into the inner image field area 34, are detected by the camera unit 30 and analyzed by the analysis and control unit 54 in a special embodiment of the process according to the present invention. The analysis and control unit 54 signals an incorrect use of the alcohol measuring device 10. This means that the test subject 50 must remain on the driver's seat 42 of the vehicle 40 (in the inner image field area 34 of the camera unit 30) during the alcohol measurement. The signal transmitter 20 provided at the alcohol measuring device 10 sends an infrared signal, which can be recorded by the camera unit 30, during the alcohol measurement. The alcohol measurement is recognized as valid by the analysis and control unit 54 if no change has been detected in the boundary area of the inner and outer image field areas 34 and 36 by the camera unit 30 for the duration of the alcohol measurement and the camera unit 30 has recorded the infrared signal within the inner image field area 34. If no infrared signal is recognized by the camera unit 30 within the inner image field area 34 and/or if a change has been recognized in the boundary area of the inner and outer image field areas 34 and 36 by the analysis and control unit 54, a new alcohol measurement can be requested by the interlock system. In case of an alcohol measurement declared as valid and if the measured alcohol level is within the allowed range, the starting means 48 of the vehicle 40 can be released and the engine can thus be started. As an alternative, it is also possible in a graduated sequence of actions to make it possible to start the vehicle 40 if the measured alcohol level is in the allowed range despite the fact that the signal of the signal transmitter 20 of the alcohol measuring device 10 has not been detected in the inner image field area 34. At least the picture of the inner image field area 34 of the camera unit 30 is detected and stored by the analysis and control unit 54 in these cases.

The incorrect use of the interlock system against the rules is documented in the process according to the present invention such that when a breach of rules is recognized either in case of an alcohol measuring device 10 not recognized in the inner image field area 34 or in case of a motion through an unallowed boundary area 38, a trigger signal is likewise sent for documenting the event by means of the camera unit 30.

In an alternative process of the further process sequence, i.e., in which release of the starting means 48 is linked exclusively with the measured value from the alcohol measurement, the use of the vehicle 40 by the test subject 50 that is potentially against the rules is documented as an event that contains a reference to this potential violation of the rules. Documentation of the event may take place, for example, by writing a text in the analysis and control unit 54.

Figure 2:
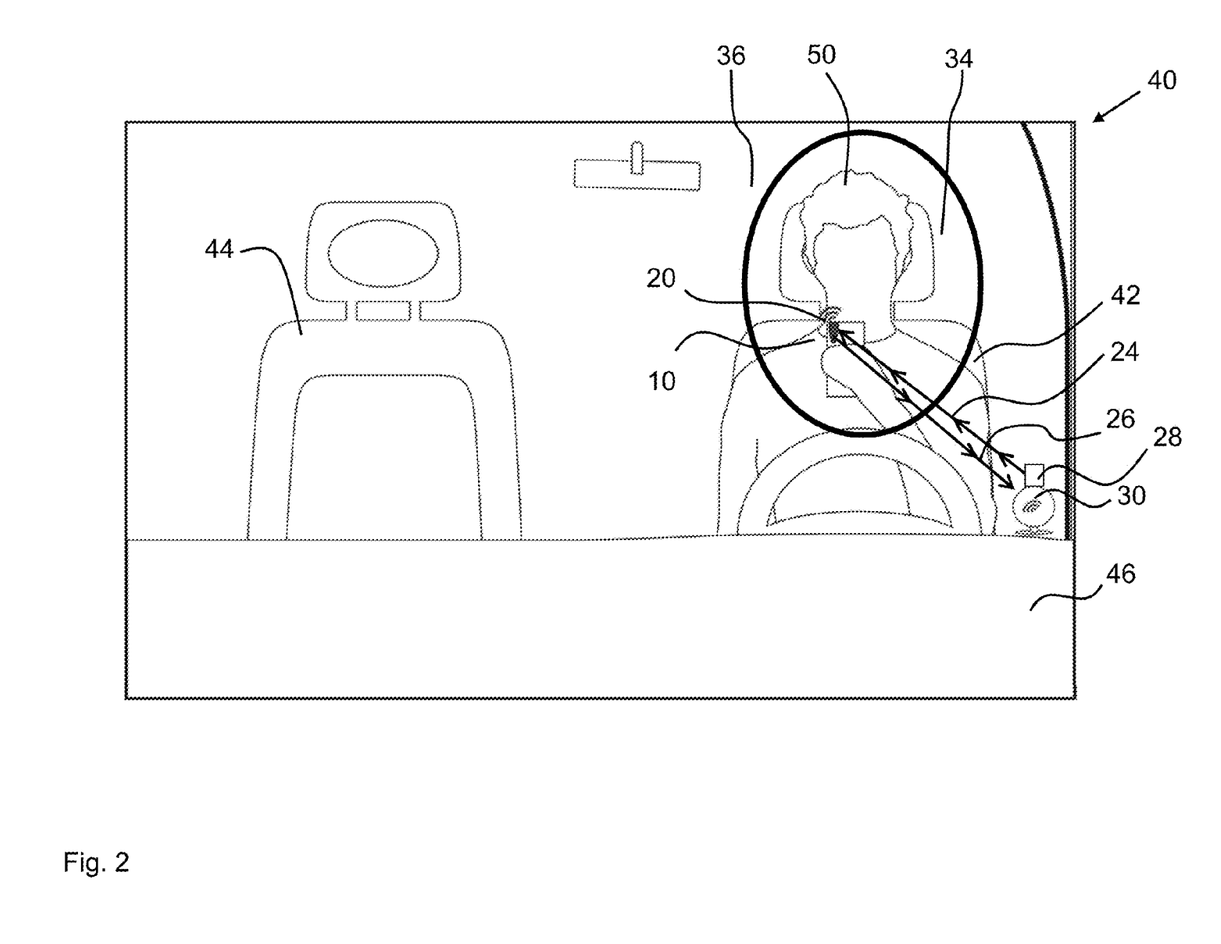
FIG. 2 is a schematic view of a second embodiment of the device according to the present invention in a vehicle.

The camera unit 30 is designed as a camera for the visible spectral range in FIG. 2. The camera unit 30 is provided with an integrated light source 28. The camera unit 30 is arranged on a dashboard 46 of the vehicle 40 and the light source 28 is directed such that it sends its light to a signal transmitter 20 designed as a light-reflecting element. The light sent by the camera unit 30 into the inner image field area 34 is reflected by the signal transmitter 20 if the alcohol measuring device 10 is present within the inner image field area 34. The reflected light can be detected by the camera unit 30. As an alternative, the light source 28 may also be provided at another location within the vehicle, for example, directly on the dashboard 46. The signal transmitter 20 may be preferably designed as an equilateral triangle, as a result of which the exact position of the alcohol measuring device can be determined by triangulation during a one-time adjustment during installation of the device according to the present invention in the vehicle 40. Signal modulation of the light signal of the light source 28 by alternatingly turning on and off does, in turn, increase the reliability of the device according to the present invention (just as in the embodiment according to FIG. 1). As an alternative to this and especially combined with a camera unit 30 for the visible spectral range, the signal transmitter 20 of the alcohol measuring device 10 may be designed to send an optical signal which alternatingly comprises red and yellow light (not shown).

As is apparent from FIGS. 1 and 2, the inner image field area 34 may have an oval shape. An oval shape in the form of an ellipse leads to good scalability and permits optimal detection of the test subject 50 in its longitudinal axis.

Figure 3:
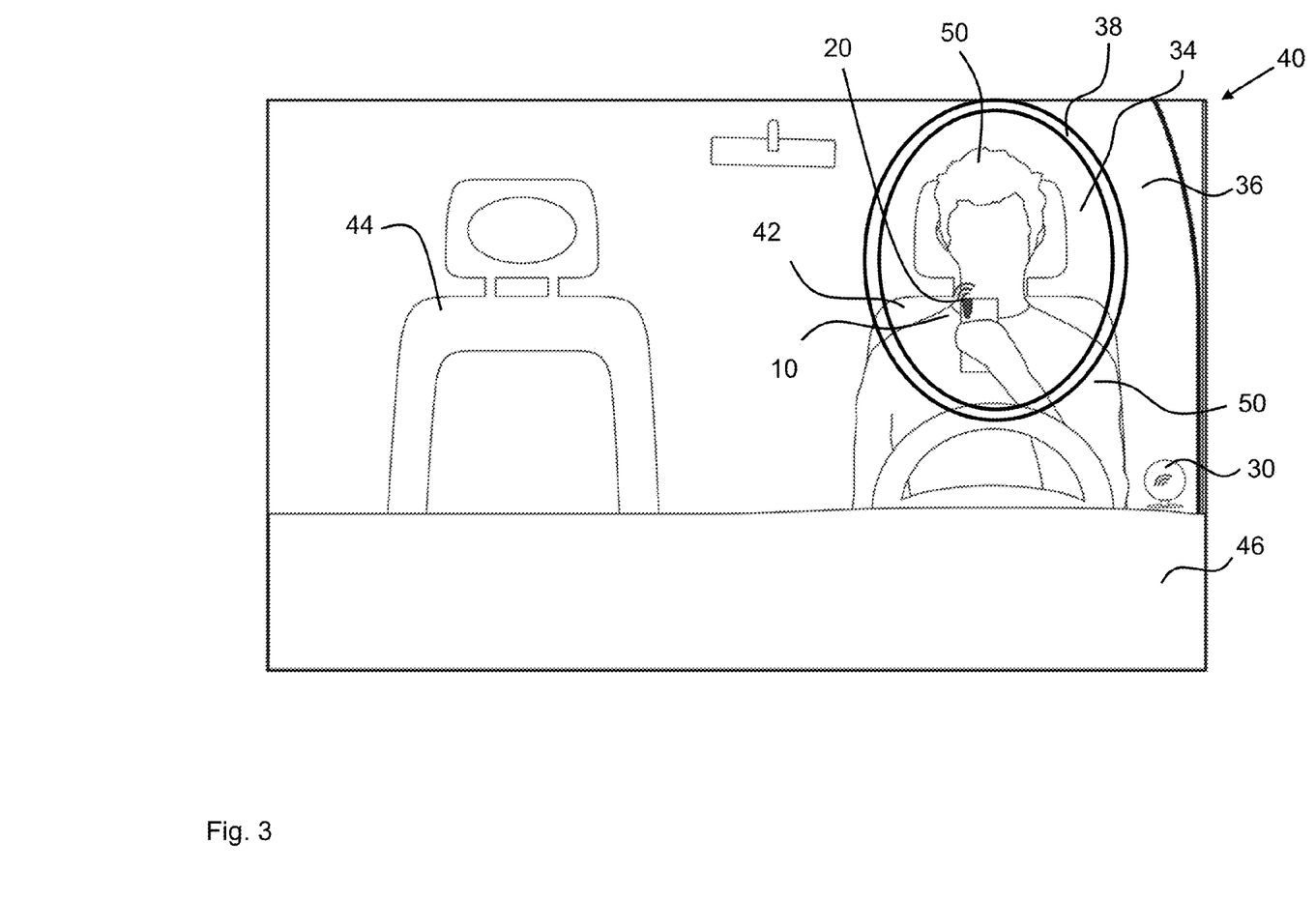
FIG. 3 is a schematic view of a third embodiment of the device according to the present invention in a vehicle.

The inner image field area 34 and the outer image field area 36 are not contiguous but have a boundary area 38 in the embodiment variant shown in FIG. 3. The boundary area 38 is preferably designed as regular strips of an oval shape around the position of the driver, i.e., the test subject 50. As an alternative to this, the boundary area 38 may also be of an irregular design. Changes within the boundary area 38 between the inner image field area 34 and the outer image field area 36 can be recorded by the camera unit 30. A motion from the outer image field area 36 through the boundary area 38 into the inner image field area 34 during the alcohol measurement can be detected and documented by the device according to the present invention.

As an alternative to the embodiments according to FIGS. 1 through 3, the camera unit 30 may also be provided in another position within the passenger compartment of the vehicle 30, for example, on a rearview mirror. In all cases, the camera unit 30 is arranged in the vehicle 40 such that it has the area of the driver's seat 42 fully in its image field 32. Besides the positions mentioned, this may also be in the area of the center console or even on the front windshield in the vicinity of the A pillar of the vehicle 40. The camera unit 30 may be fixed such that it is firmly adjusted during the period during which the interlock system is installed in the vehicle 40, but it can be removed without visible traces after the end of the installation period. The camera unit should preferably have a sealing bonded connection at the site to which it is fastened.

Figure 4:
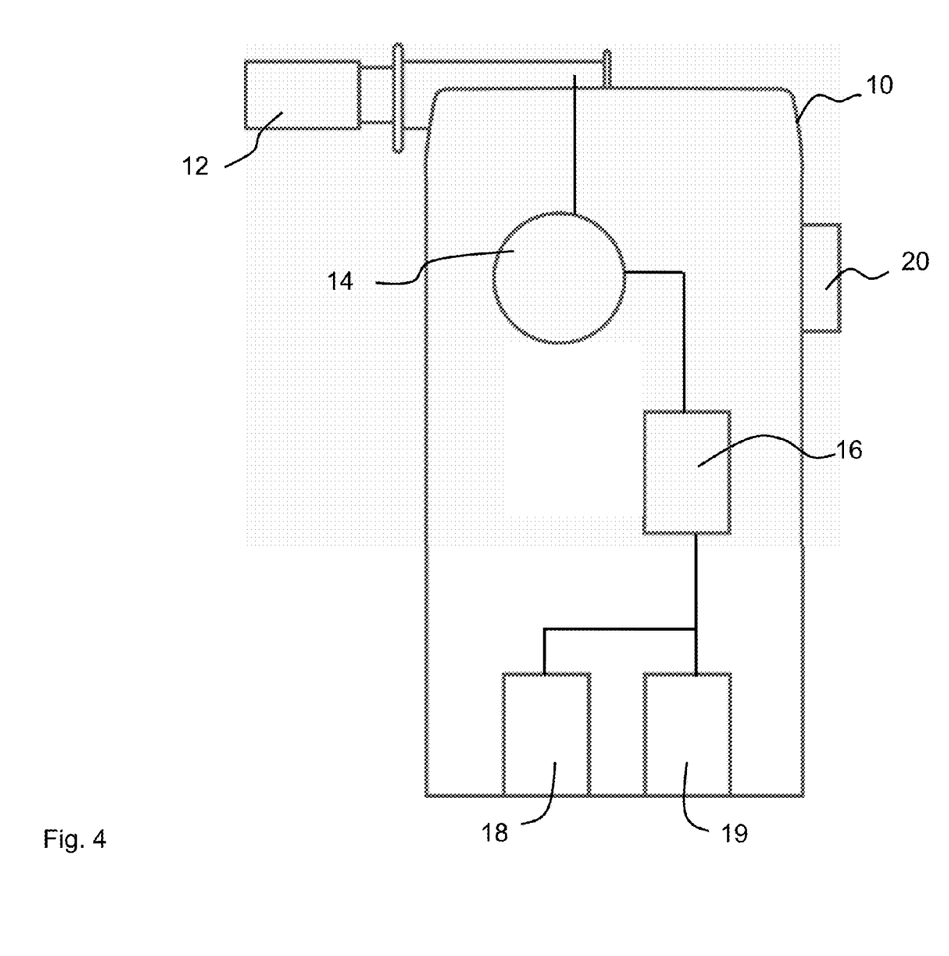
FIG. 4 is a schematic view of a breath alcohol measuring device with a signal transmitter according to the invention.

FIG. 4 shows a schematic view of an alcohol measuring device 10. The alcohol measuring device 10 is designed as a breath alcohol measuring device, which measures the breath alcohol concentration of a test subject 50. The test subject 50 provides for this a breath sample into the alcohol measuring device 10 through a mouthpiece 12, and the breath alcohol concentration is measured with an electrochemical sensor 14 and a downstream measuring analysis means 16. The signal transmitter 20 is provided on the opposite side of the mouthpiece 12. Furthermore, the alcohol measuring device 10 has a communications connection for a cable mount 18 and/or a communications connection for radio communication 19 to the analysis and control unit 54. All relevant events, for example, date, time, performance or denial of an alcohol measurement, measured alcohol concentrations as well as an incorrect use of the alcohol measuring device 10 are recorded in a memory unit 56 (shown in FIG. 5) during the use of the vehicle 40 by the test subject 50. The memory unit 56 is preferably connected to the analysis and control unit 54 or is preferably integrated in same.

In another embodiment, the complete interlock system may be connected, by means of a wireless communication system, to a central memory unit, to which the data are transmitted at regular intervals. Criteria for the transmission may be both time intervals, for example, days, or the amount of data stored in the storage unit 56 integrated in the vehicle 40 or a combination of the two.

The use of the device according to the present invention combined with an interlock system in a vehicle 40 represents only one embodiment variant. As an alternative to this, the device according to the present invention may be integrated in an access control for industrial safety zones, for example, in the chemical industry, or also, for example, for releasing a control panel of a machine.

While the present invention has been described with reference to the preferred exemplary embodiments, various changes and modifications are clear to the person skilled in the art. All these changes and modifications shall fall within the scope of protection of the claims attached. While specific embodiments of the invention have been shown and described in detail to illustrate the application of the principles of the invention, it will be understood that the invention may be embodied otherwise without departing from such principles.

LIST OF REFERENCE NUMBERS

10 Alcohol measuring device
12 Mouthpiece
14 Sensor
16 Measuring analysis means
18 Communications connection for cable mounting
19 Communications connection for wireless communication with the analysis and control unit
20 Signal transmitter
22 Light-reflecting element 24 Transmitted signal
26 Reflector signal
28 Light source
30 Camera unit
32 Image field of the camera unit
34 Inner image field area
36 Outer image field area
38 Boundary area
40 Vehicle
42 Driver's seat
44 Front passenger seat
46 Dashboard
48 Starting means
50 Test subject
52 Requesting unit
54 Analysis and control unit
56 Memory unit
58 Transmitting and receiving unit

What is claimed is:

1. A device for recognizing a correct use of an alcohol measuring device by a test subject, the device comprising:
an alcohol measuring device for administering an alcohol measurement, the alcohol measurement having a duration;
a camera unit with a camera unit image field corresponding to a predetermined face area of the test subject, said camera unit configured to register the camera unit image field with the predetermined face area of the test subject;
a signal transmitter having a position linked to a position of said alcohol measuring device configured to send a light signal that can be detected by the camera unit, said camera unit configured to detect the signal sent by said signal transmitter within said camera unit image field;
wherein the light signal is selected from the group consisting of visible light and infrared light;
an analysis and control unit operatively connected to the alcohol measuring device and operatively connected to the camera unit, the analysis and control unit being configured to receive and analyze said light signal sent by said signal transmitter in the camera unit image field area during the alcohol measurement; and
wherein the analysis and control unit is configured to receive a camera communication from the camera unit that the camera unit has detected the light signal during or before the duration and receives an alcohol measurement device communication from the alcohol measurement device.

2. A device in accordance with claim 1, wherein the alcohol measuring device includes breath alcohol measuring means for measuring an alcohol content of a breath sample provided by the test subject.

3. A device in accordance with claim 1, wherein said camera unit comprises an infrared camera and said signal transmitter sends an infrared signal where the infrared signal is preferably a variable or modulated infrared signal or an infrared signal switched on and off alternatingly.

4. A device in accordance with claim 1, wherein the camera unit operates in the visible spectral range.

5. A device in accordance with claim 4, wherein the signal transmitter includes optical transmission means for sending an optical signal or a light-reflecting element for reflecting an optical signal provided by a light source for illuminating the signal transmitter.

6. A device in accordance with claim 4, wherein said optical transmission means sends alternatingly red and yellow light.

7. A device in accordance with claim 1, wherein the inner image field area of the camera unit has an oval shape.

8. A device in accordance with claim 1, wherein:
the camera unit image field is divided into the inner image field area and an outer image field area; and
the camera unit detects motions from the inner image field area to the outer image field area and/or from the outer image field area to the inner image field area, and the analysis and control unit analyzes data received from the camera unit relating to the motions.

9. A device in accordance with claim 8, wherein the outer image field area of the camera unit has an oval shape.

10. A device in accordance with claim 8, wherein a boundary between the inner image field area and the outer image field area is designed as a boundary area and the inner image field area completely covers an area of a driver's seat.

11. A device in accordance with claim 1, further comprising a memory unit provided for recording images of the camera unit image field.

12. A system for recognizing a correct use of an alcohol measuring device by a test subject and for checking an alcohol content of the test subject, the system comprising:
an alcohol measuring device for administering an alcohol measurement, the alcohol measurement having a duration,
a camera unit with a camera unit image field corresponding to a predetermined face area of the test subject, wherein the camera unit is configured to register a predetermined face area of the test subject,
a signal transmitter having a position linked to a position with said alcohol measuring device, the signal transmitter configured to send a light signal, said camera unit detecting said light signal when said signal transmitter is in said camera unit image field,
wherein the predetermined light signal is selected from the group consisting of visible light and infrared light;
an analysis and control unit operatively connected to the alcohol measuring device and operatively connected to the camera unit, said analysis and control unit being configured to receive and analyze said light signal sent by said signal transmitter in the camera unit image field;
wherein the analysis and control unit is configured to receive a camera communication from the camera unit that the camera unit has detected the light signal during or before the duration and receives an alcohol measurement device communication from the alcohol measurement device; and
a vehicle with a driver's seat and with a vehicle immobilizer, said vehicle immobilizer being in connection with the alcohol measuring device, the camera unit being arranged in the vehicle such that the camera unit image field covers an area of said driver's seat.

13. A system in accordance with claim 12, wherein the alcohol measuring device includes breath alcohol measuring means for measuring an alcohol content of a breath sample provided by the test subject.

14. A system in accordance with claim 13, wherein:
said signal transmitter sends one or more of an infrared signal and/or a visible optical signal; and
the camera unit detects the infrared signal and/or the visible optical signal within the camera unit image field or detects no infrared signal and/or no visible optical signal within the camera unit image field during an alcohol measurement.

15. A system in accordance with claim 12, wherein the camera unit detects changes within the camera unit image field during an alcohol measurement, and the analysis and control unit analyzes data received from the camera unit relating to the changes.

16. A process for recognizing a correct use of an alcohol measuring device by a test subject, the process comprising the steps of:
providing a camera unit with a camera unit image field corresponding to a predetermined face area of the test subject, wherein the camera unit is configured to register a predetermined face area of the test subject;
recording the camera unit image field with the camera unit at a beginning of an alcohol measurement, the alcohol measurement having a duration;
providing a signal transmitter having a position linked to a position of said alcohol measuring device;
sending a light signal during the alcohol measurement from the signal transmitter, which signal can be recorded by the camera unit;
wherein the light signal is selected from the group consisting of visible light and infrared light;
providing an analysis and control unit connected to the alcohol measuring device and connected to the camera unit;
analyzing the light signal with the analysis and control unit;
receiving, with the analysis and control unit, a camera communication from the camera unit that the camera unit has detected the light signal during or before the duration; and
receiving, with the analysis a control unit, an alcohol measurement device communication from the alcohol measurement device.

17. A process in accordance with claim 16, wherein the camera unit is activated at least one of prior to the alcohol measurement and after initiating a vehicle starting operation.

18. A process in accordance with claim 16, wherein a number of persons is detected by the camera unit in the camera unit image field in the step of recording the camera unit image field with the camera unit at the beginning of an alcohol measurement and a signal is sent and/or the alcohol measurement is not started if more than one person is detected in the inner image field area.

19. A process in accordance with claim 16, wherein in the step of sending a light signal during the alcohol measurement from the signal transmitter, which signal can be recorded by the camera unit, the signal transmitter sends an infrared signal, including one of a variable or modulated infrared signal and a turned alternatingly on and off signal, or sends at least one light signal including one of an alternatingly red and yellow light signal and a variable light intensity light signal.

20. A process in accordance with claim 16, wherein the camera unit detects changes in the camera unit image field starting from the beginning of the alcohol measurement and the analysis and control unit analyzes the changes.

* * * * *